Oct. 27, 1970 G. DELBARD Plant Pat. 2,995
ROSE PLANT
Filed Jan. 6, 1969
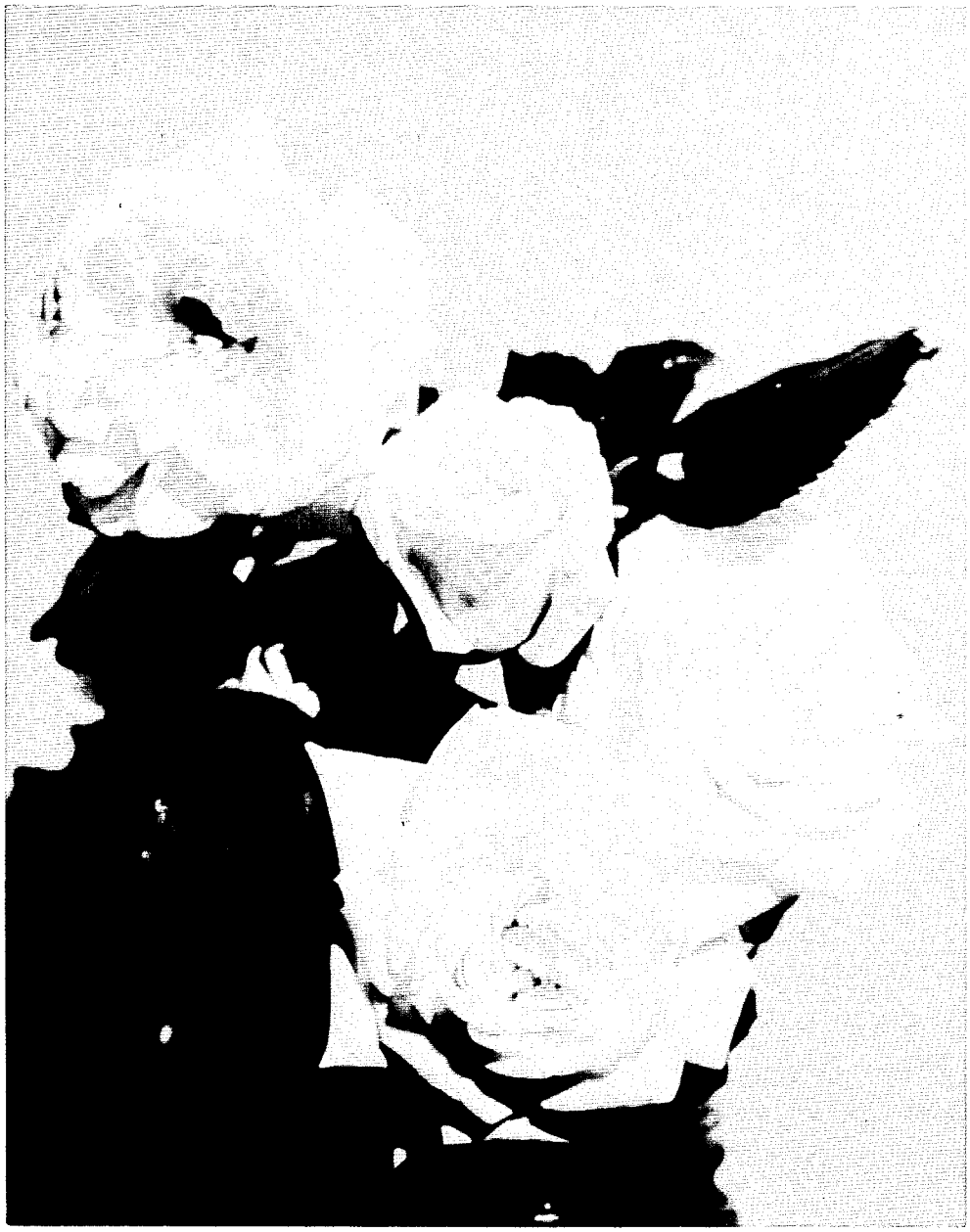
Inventor.
Georges Delbard
By: Robb & Robb
Attorneys.

United States Patent Office

Plant Pat. 2,995
Patented Oct. 27, 1970

2,995
ROSE PLANT

Georges Delbard, Allier, France, assignor, by mesne assignments, to Stark Bro's Nurseries & Orchards Co., Louisiana, Mo., a corporation of Missouri

Filed Jan. 6, 1969, Ser. No. 789,426
Int. Cl. A01h *5/00*
U.S. Cl. Plt.—15 1 Claim

The present invention relates to a new and distinct variety of rose plant of the hybrid tea class, which was orginated by me by crossing an unnamed and unpatented seedling of the rose variety known as "Orleans" (unpatented) X the rose variety known as "Goldilocks" U.S. Plant Pat. No. 672) with an unnamed and unpatented seedling of the rose variety known as "Fashion" (U.S. Plant Pat. No. 789) X an unnamed and unpatented seedling of unknown parentage.

As the result of this breeding, I have produced a new and improved rose variety which generally resembles the variety "Goldilocks," but which is distinguished therefrom and from all other rose varieties of which I am aware, as evidenced by the following unique combination of characteristics which are outstanding in the new variety and represent improvements over "Goldilocks":

(1) A more vigorous plant habit;

(2) More abundant and more glossy, deep green foliage which is more resistant to blackspot;

(3) An earlier spring blooming habit, with the blooms being abundant and continuing later in the fall;

(4) Attractive and more slowly-opening buds which remain in a partially open stage for prolonged periods of time; and (5) A distinctive, attractive and deeper yellow flower color which fades less and only slightly in hot weather.

Asexual reproduction of my new variety by budding, as performed by me in France and also performed on my behalf at Louisiana, Mo., U.S.A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the British Horticultural Colour Chart, except where general color terms of ordinary dictionary significance are obvious:

Type: Hardy; bush.
Class: Hybrid tea.
Breeding: Seedling.
*Seed parent.*—An unnamed seedling of "Orleans" X "Goldilocks."
*Pollen parent.*—An unnamed seedling of "Fashion" X an unnamed seedling of unknown parentage.
Progagation: Holds its distinguishing characteristics through succeeding propagations by budding.

FLOWER (Observations made from specimens grown at Louisiana, Mo., U.S.A.)

Continuity: Continuous.
Fragrance: Moderate.
*Nature.*—Spicy.
Flowers borne: Usually singly; on short to medium length stems of normal strength.
Quantity of bloom: Abundant, outdoors.

Bud:
*Peduncle.*—Medium length; heavy; bending; stiff; almost smooth; few thorns. Color—Erythrite Red, Plate 0027/1, p. 190, vol. II.
*Before Calyx breaks.*—Size—from medium to small. Form—pointed; with a conspicuous neck; with foliaceous appendages; with much-cut, bristle-like foliaceous parts extending beyond the tip of the bud equal to ½ or more of its length. Color—Lemon Yellow, Plate 4, p. 4, vol. I.
*As calyx breaks.*—Color—Lemon Yellow, Plate 4, p. 4, vol. I.
almost smooth; few thorns. Color—Erythrite Red,
*As first petal opens.*— Size—from small to medium. Form—globular. Color—outside: Lemon Yellow, Plate 4/2, p. 4, vol. I; inside—Lemon Yellow, Plate 4/1, p. 4, vol. I.
*Opening.*—Opens up well.

Bloom:
*Size (when fully open).*—Medium large; from 2¼ inches to 3¾ inches.
*Petalage.*—Very double; from 50 to 60 petals; arranged regularly.
*Form.*—Full-centered at first and becoming high-centered; petals being at first tightly rolled outward but later becoming loosely rolled outward at maturity.

Petals:
*Texture.*—Thick; soft.
*Appearance.*—Inside—velvety. Outside—satiny.
*Shape.*—Outside—round, with apex flat and with 1 notch. Intermediate—obovate, with apex flat and with 1 notch. Inside—obovate; irregular; with 1 notch.

This description if a newly opened flower was made from a rose grown outdoors during the month of October at Louisiana, Mo., U.S.A.:

*Color.*—Outer petal—outside surface: Lemon Yellow, Plate 4/1, p. 4, vol. I; inside surface: Lemon Yellow, Plate 4/2, p. 4, vol. I. Intermediate petal—outside surface: Lemon Yellow, Plate 4/1, p. 4, vol. I; inside surface—Lemon Yellow, Plate 4/2, p. 4, vol. I. Inner petal— outside surface: Lemon Yellow, Plate 4/1, p. 4, vol. I; inside surface—Lemon Yellow, Plate 4/2, p. 4, vol. I.

This description was made from a rose that was open for three days outdors during the month of October at Louisiana, Mo., U.S.A.:

*Color.*—Outer petal—outside surface: Lemon Yellow, Plate 4/2, p. 4, vol. I; inside surface: Lemon Yellow, Plate 4/2, p. 4, vol. I. Inner petal—outside surface: Lemon Yellow, Plate 4/1, p. 4, vol. I; inside surface—Lemon Yellow, Plate 4/1, p. 4, vol. I.
*General color effect.*—Newly opened flower—bright deep yellow. 3-days open—bright yellow.
*Behavior.*—Persist; fades slightly in hot, dry weather.
*Flower longevity.*—On bush in garden—5 days in October. Cut roses grown outdoors and kept at livingroom temperatures—4 days in October.

REPRODUCTIVE ORGANS

Stamens: Many; regularly arranged about pistils.
Filaments: From short to medium length; all with anthers.
*Color.*—Lemon Yellow, Plate 4/3, p. 4, vol. I.
Anthers: Medium large; all open at once.
*Color.*—Lemon Yellow, Plate 4, p. 4, vol. I.

Pollen: Sparse.

*Color.*—Tangerine Orange, Plate 4, p. 9, vol. I.

Styles: Even; medium long; medium thin; bunched.

Stigma:

*Color.*—Lemon Yellow, Plate 4/1, p. 4, vol. I.

Ovaries: All enclosed in calyx.

Hips: Short; flat.

*Color.*—Scheele's Green, Plate 860/3, p. 175, vol. II.

Sepals: Permanent; long.

*Color.*—Scheele's Green, Plate 860/1, p. 175, vol. II.

Seeds: Few, small.

PLANT

Foliage:

*Leaves.*—Compound of 5 leaflets; abundant; moderately small; moderately heavy; glossy.

*Leaflets.*—Shape—oval. Apex—acute. Base—round. Margin—simply serrate.

*Color.*—Mature—upper surface: Ivy Green, Plate 0001060/3, p. 200, vol. II; under surface: Spinach Green, Plate 0960/3, p. 187, vol. II. Young—upper surface: Spinach Green, Plate 0960/1, p. 187, vol. II; under surface—Scheele's Green, Plate 860/1, p. 175, vol. II.

*Rachis (the supporting stem of the compound leaf).*—Medium light. Upper side—grooved. Under side—sparsely thorny.

*Stipules.*—Medium long; medium narrow; with short points turning out at an angle of more than 45°.

*Disease resistance.*—Moderately resistant to blackspot, as determined by comparison with other varities grown under the same conditions at Louisiana, Mo., U.S.A.

Growth:

*Habit.*—Bushy, upright; much-branched.

*Growth.*—Moderate.

*Canes.*—Moderately heavy.

*Main stems.*—Color—bright Spinach Green, Plate 0960, p. 187, vol. II. Thorns—many; straight; with long, narrow base. Prickles—none. Hairs—none.

*Branches.*—Color — bright Spinach Green, Plate 0960/1, p. 187, vol. II. Thorns—many; long; straight; with long, narrow base. Prickles—none. Hairs—none.

*New shoots.*—Color—Bright Spinach Green, Plate 0960/3, p. 187, vol. II. Thorns—many; long; straight; with long, narrow base. Prickles—none. Hairs—none.

I claim:

1. A new and distinct variety of rose plant of the hybrid tea class, substantially as herein shown and described, characterized particularly as to novelty by its general resemblance to the rose variety "Goldilocks" (U.S. Plant Pat. No. 672), but being particularly distinct therefrom by a more vigorous plant habit, more abundant and more glossy, deep green foilage which is more resistant to blackspot, an earlier spring blooming habit, with the blooms being abundant and continuing later in the fall, attractive and more slowly-opening buds which remain in a partially open stage for prolonged periods of time, and a distinctive, attractive and deeper yellow flower color which fades less and only slightly in hot weather.

No references cited.

ROBERT E. BAGWILL, Primary Examiner